(12) United States Patent
Liang et al.

(10) Patent No.: US 8,703,786 B2
(45) Date of Patent: Apr. 22, 2014

(54) ETRAVIRINE FORMULATIONS AND USES THEREOF

(71) Applicants: Dong Liang, Pearland, TX (US); Mathew Kizhakkekara Joseph, Houston, TX (US); Jyothy John, Houston, TX (US); Cyril V Abobo, Richmond, TX (US)

(72) Inventors: Dong Liang, Pearland, TX (US); Mathew Kizhakkekara Joseph, Houston, TX (US); Jyothy John, Houston, TX (US); Cyril V Abobo, Richmond, TX (US)

(73) Assignee: Texas Southern University, Houston, TX (US)

( * ) Notice: Subject to any disclaimer, the term of this patent is extended or adjusted under 35 U.S.C. 154(b) by 0 days.

(21) Appl. No.: 13/707,122

(22) Filed: Dec. 6, 2012

(65) Prior Publication Data

US 2013/0150389 A1 Jun. 13, 2013

Related U.S. Application Data

(60) Provisional application No. 61/568,001, filed on Dec. 7, 2011.

(51) Int. Cl.
*A61K 31/505* (2006.01)
*A61K 9/00* (2006.01)

(52) U.S. Cl.
USPC .................................. 514/272; 424/400

(58) Field of Classification Search
None
See application file for complete search history.

(56) References Cited

U.S. PATENT DOCUMENTS

2006/0258698 A1* 11/2006 Mudumba et al. ............ 514/291
2007/0219243 A1* 9/2007 Kearney et al. ............... 514/312
2010/0143454 A1* 6/2010 McLinden et al. ............ 424/450

* cited by examiner

*Primary Examiner* — Ernst Arnold
*Assistant Examiner* — Jianfeng Song
(74) *Attorney, Agent, or Firm* — Benjamin Aaron Adler (57) ABSTRACT

Provided herein is a pharmaceutical formulation of etravirine, said formulation comprising: etravirine; a dipolar aprotic solvent; a non-ionic water dispersible surfactant; and water. Further provided is a pharmaceutical formulation of etravirine, said formulation comprising: etravirine; a non-ionic water dispersible surfactant; and water.

28 Claims, 2 Drawing Sheets

ETRAVIRINE FORMULATIONS AND USES THEREOF

CROSS-REFERENCE TO RELATED APPLICATIONS

This non-provisional application claims benefit of priority under 35 U.S.C. §119(e) of provisional application U.S. Ser. No. 61/568,001, filed Dec. 7, 2011, now abandoned, the entirety of which is hereby incorporated by reference.

BACKGROUND OF THE INVENTION

1. Field of the Invention

The present invention relates to the field of pharmaceutical formulations of a non-nucleoside reverse transcriptase inhibitor. More specifically, the present invention relates to novel formulations of etravirine and uses thereof.

2. Description of the Related Art

Non-nucleoside reverse transcriptase inhibitors are a key component of highly active antiretroviral therapy (HAART) because of their ability to target an allosteric binding pocket on the reverse transcriptase enzyme giving rise to a broad spectrum of activity against Human Immunodeficiency Virus (HIV) reverse transcriptase mutations. HAART has been the standard of care for HIV infection since 1996 and has resulted in substantial increases in survival. Diarylpyrimidine compounds represent second-generation non-nucleoside reverse transcriptase inhibitors and are useful for treatment of HIV infected patients with non-nucleoside reverse transcriptase inhibitor-resistant viruses.

Etravirine (I), formerly TMC 125 and chemically known as 4-[[6-amino-5-bromo-2-[(4-cyanophenyl)amino]-4-pyrimidinyl]oxy]-3,5-dimethyl benzonitrile, is an non-nucleoside reverse transcriptase inhibitor approved in 2008 for use in combination with other antiretroviral agents in treatment-experienced adult patients with multidrug-resistant HIV infections. Etravirine is marketed worldwide as an oral tablet and was first disclosed by De Corte et al. in U.S. Pat. No. 7,037,917.

Etravirine is the first drug in the second generation of non-nucleoside reverse transcriptase inhibitors and has been recently marketed for the treatment of HIV infection (1). Etravirine is more potent than other first generation non-nucleoside reverse transcriptase inhibitors due to its activity against non-nucleoside reverse transcriptase inhibitor-resistant HIV-1 (2). The recommended dose of this drug is 200 mg (or two 100 mg tablets) taken twice daily following a meal (3).

Etravirine is highly bound to plasma proteins and is primarily metabolized by cytochrome P450 CYP 3A4, 2C9, and 2C19 enzymes. According to the Biopharmaceutics Classification System, etravirine is a class IV compound (low water solubility and permeability). This highly lipophilic drug contains an octanol:water partition coefficient (logP) greater than 5, along with an ionization constant (pka) of 3.75 (4). Despite the use of etravirine in the clinical management of HIV infected patients, limited pharmacokinetic information is available regarding the absorption, distribution, metabolism, and excretion following oral administration (5).

There is a need in the art for an oral liquid dosage formulation, especially for those AIDS patients who are often unable to swallow a pill. There is, furthermore, a need to develop a more bioavailable formulation of etravirine to facilitate better clinical outcomes. The prior art is deficient in improved etravirine oral formulations and uses thereof. The present invention fulfils this longstanding need in the art.

SUMMARY OF THE INVENTION

Based on in vitro experiments, etravirine is thought to be absorbed via a passive transcellular diffusion mechanism. Moreover, etravirine is an inhibitor of p-gp with an apparent $IC_{50}$ value of 24.2 µM. Etravirine is absorbed slowly, with median peak concentration occurring at approximately 4.0 hours (2 to 6 hours depending on the formulation) after fasted oral administration. The absolute bioavailability of etravirine has not been determined because of the lack of an intravenous formulation (6). In vivo, etravirine is an inducer of CYP3A4 and an inhibitor of the CYP2C subfamily (7). Etravirine has a terminal elimination half-life in plasma of approximately 30-40 h. The drug should be taken following a meal to enhance bioavailability (8). Etravirine has low solubility and permeability and is categorized as a Class IV compound according to the Bio-pharmaceutics Classification System (9).

Currently, most of the marketed anti-AIDS medications are solid dosage forms and there is a need for a non-nucleoside reverse transcriptase inhibitor liquid formulation for better patient compliance and especially for those patients who have difficulty in swallow pills. Due to the poor water solubility of etravirine, the present invention provides the development of a water soluble and stable etravirine liquid dosage formulation that is suitable for oral administration. Oral bioavailability of the formulation of the present invention was also compared with the commercial Intelence® 100 mg Tablets.

The present invention describes the development of clinically applicable oral liquid dosage formulations of etravirine. Thus, in one embodiment, the present invention provides a pharmaceutical formulation of etravirine, said formulation comprising: etravirine; a dipolar aprotic solvent; a non-ionic water dispersible surfactant; and water.

In another embodiment, the present invention provides a pharmaceutical formulation of etravirine, said formulation comprising: etravirine; a non-ionic water dispersible surfactant; and water.

In yet another embodiment, the present invention provides a pharmaceutical formulation of etravirine, said formulation comprising: etravirine; 1-methyl-2-pyrrolidinone; a non-ionic water dispersible surfactant; and water.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "individual" refers to a mammal, preferably a human, which is the recipient of any pharmaceutical formulation of etravirine or other drug, therapeutic or compound described herein.

Etravirine is the first drug in the second generation of non-nucleoside reverse transcriptase inhibitors (NNRTIs) and has been recently marketed as Intelence® 100 mg or 200 mg tablets for the treatment of HIV infection. Etravirine is more effective than the first generation non-nucleoside reverse transcriptase inhibitors due to its activity against non-nucleoside reverse transcriptase inhibitor-resistant HIV-1. The recommended dose of this drug is 200 mg (or two 100 mg tablets) taken twice daily following a meal. Etravirine is a class IV compound, i.e., it has low water solubility and low gastrointestinal permeability. Despite its use in the clinical management of HIV infected patients, the drug has very limited bioavailability. All currently available anti-AIDS drugs in the U.S. market are solid dosage forms.

The present invention provides a co-solvent dosage formulation of etravirine suitable for oral administration. The formulation contains 5 mg/mL of etravirine dissolved in 3.5% 1-methyl-2-pyrrolidinone, 46.5% Labrasol, and 50% water. The formulation was found to be stable after 9 month storage at room temperature. The drug formulation was successfully administered to rats without any signs of acute toxicity. A pharmacokinetic study also demonstrated that the formulation of the present invention had an over 40-fold superior bioavailability when compared to the commercially available Intelence® Tablet formulation. This formulation of the present invention significantly increased oral bioavailability of the drug by over 40-fold when compared with the marketed Intelence® Tablet.

Thus, the present invention is directed to a pharmaceutical formulation of etravirine, the formulation comprising: etravirine; a dipolar aprotic solvent; a non-ionic water dispersible surfactant; and water. Preferably, the etravirine is contained in said formulation in a concentration range of from about 5 mg/mL to about 10 mg/mL. Representative dipolar aprotic solvents include but are not limited to 1-methyl-2-pyrrolidinone, dimethylformamide, dimethylacetamide, ethanol and dimethyl sulfoxide. In one preferred embodiment, the dipolar aprotic solvent is 1-methyl-2-pyrrolidinone which is contained in the formulation in a concentration of from about 0.5% to about 10%. If dimethylformamide is the dipolar aprotic solvent, it may be contained in the formulation in a concentration of from about 0.5% to about 10%. If dimethylacetamide is the dipolar aprotic solvent, it may be contained in the formulation in a concentration of from about 0.5% to about 10%. If dimethyl sulfoxide is the dipolar aprotic solvent, it may be contained in the formulation in a concentration of from about 0.5% to about 10%. If ethanol is the dipolar aprotic solvent, it may be contained in the formulation in a concentration of from about 0.5% to 25%. Generally, the nonionic surfactant comprises polyethylene glycol esters, a glyceride fraction and free polyethylene glycol. Representative nonionic surfactants include but are not limited to caprylocaproyl macrogol-8 glyceride, polyethoxylated castor oil such as polyoxyl 40 hydrogenated castor oil (Cremophor RH 40), polyoxyl 60 hydrogenated castor oil (Cremophor RH 60), polyoxyl 35 castor oil (Cremophor EL), polyoxyl 5 castor oil, polyoxyl 9 castor oil, polyoxyl 15 castor oil, and d-α-tocopheryl polyethylene glycol 1000 succinate (TPGS), polyethylene glycol (15)-hydroxystearate (Solutol HS-15), PEG 300 caprylic/capric glycerides (Softigen 767). Preferably, the caprylocaproyl macrogol-8 glyceride is contained in the formulation in a concentration of from about 40% to about 50%. Even more preferably, the caprylocaproyl macrogol-8 glyceride is contained in the formulation in a concentration of from about 46%. In one preferred aspect of the pharmaceutical formulation, the formulation contains 5 mg/mL of etravirine dissolved in 3.5% 1-methyl-2-pyrrolidinone, 46.5% caprylocaproyl macrogol-8 glyceride, and 50% water. Generally, the pharmaceutical formulation is suitable for oral administration.

The present invention is further directed to a pharmaceutical formulation of etravirine, said formulation comprising: etravirine; a non-ionic water dispersible surfactant; and water. Preferably, the etravirine is contained in said formulation in a concentration range of from about 3 mg/mL to about 8 mg/mL. The nonionic surfactant typically comprises polyethylene glycol esters, a glyceride fraction and free polyethylene glycol. Representative nonionic surfactant include but are not limited to caprylocaproyl macrogol-8 glyceride, polyethoxylated castor oil such as polyoxyl 40 hydrogenated castor oil (Cremophor RH 40), polyoxyl 60 hydrogenated castor oil (Cremophor RH 60), polyoxyl 35 castor oil (Cremophor EL), polyoxyl 5 castor oil, polyoxyl 9 castor oil, polyoxyl 15 castor oil, and d-α-tocopheryl polyethylene glycol 1000 succinate (TPGS), Solutol HS-15, PEG 300 caprylic/capric glycerides (Softigen 767). Preferably, the caprylocaproyl macrogol-8 glyceride is contained in said formulation in a concentration of from about 40% to about 55%. Even more preferably, the caprylocaproyl macrogol-8 glyceride is contained in said formulation in a concentration of from about 45-50%. For example, the formulation may contain 5 mg/mL of etravirine dissolved in 50% caprylocaproyl macrogol-8 glyceride, and 50% water. As described, this pharmaceutical formulation is suitable for oral administration. In a related embodiment, this pharmaceutical formulation may further comprise a dipolar aprotic solvent. Representative dipolar aprotic solvents include but are not limited to 1-methyl-2-pyrrolidinone, dimethylformamide, dimethylacetamide, ethanol and dimethyl sulfoxide. For example, 1-methyl-2-pyrrolidinone may be contained in said formulation in a concentration of from about 0.5% to about 10%, dimethylformamide may be contained in said formulation in a concentration of from about 0.5% to about 10%, dimethylacetamide may be contained in said formulation in a concentration of from about 0.5% to about 10%, dimethyl sulfoxide may be contained in said formulation in a concentration of from about 0.5% to about 10%, ethanol may be contained in said formulation in a concentration of from about 0.5% to about 25%.

The present invention is further directed to a pharmaceutical formulation of etravirine, said formulation comprising: etravirine; 1-methyl-2-pyrrolidinone; a non-ionic water dispersible surfactant; and water. The etravirine may be contained in the formulation in a concentration range of from about 5 mg/mL to about 10 mg/mL. In this pharmaceutical formulation, said 1-methyl-2-pyrrolidinone may be contained in the formulation in a concentration of from about 0.5% to about 10%. The nonionic surfactants are described above. For example, caprylocaproyl macrogol-8 glyceride may be contained in said formulation in a concentration of from about 40% to about 50%. Preferably, the caprylocaproyl macrogol-8 glyceride is contained in said formulation in a concentration of from about 46%.

Figure 1:
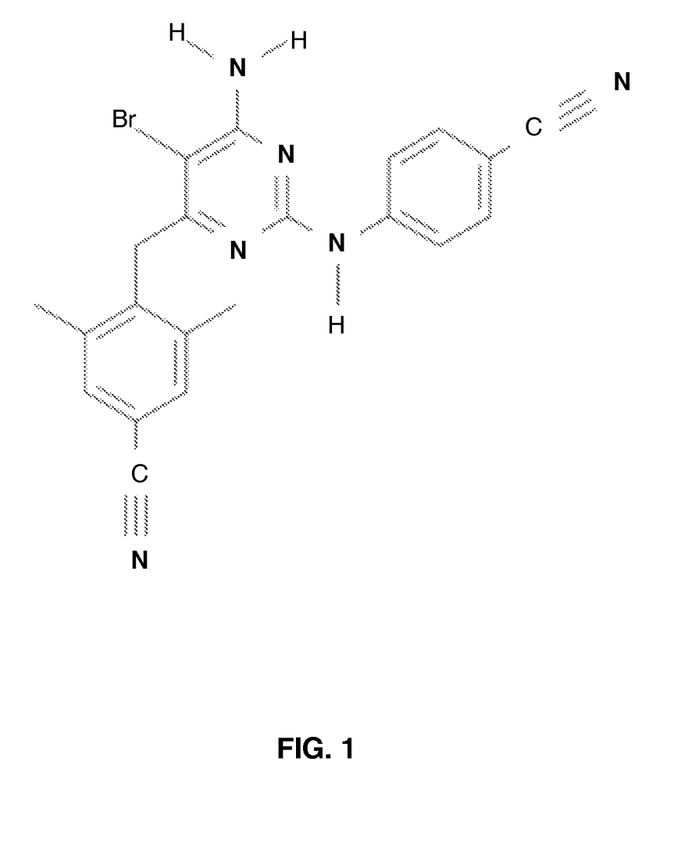
FIG. 1 shows the chemical structure of etravirine.

N-Methyl-2-pyrrolidinone (NMP; FIG. 1) is a chemical compound with 5-membered lactam structure. It is a clear to slightly yellow liquid miscible with water and solvents like ethyl acetate, chloroform, benzene and lower alcohols or ketones. It also belongs to the class of dipolar aprotic solvents which also includes dimethylformamide, dimethylacetamide and dimethyl sulfoxide. Other names for this compound are: 1-methyl-2-pyrrolidinone, N-methyl-2-pyrrolidinone, 1-methyl-2-pyrrolidone and m-pyrrole, and pharmasolve.

The following examples are given for the purpose of illustrating various embodiments of the invention and are not meant to limit the present invention in any fashion.

Example 1

Chemicals and Reagents

Etravirine standard powder (98% pure, Lot#10-ABY-54, MW=435.28) was purchased from Toronto Research Chemicals Inc. (Ontario, Canada). Intelence® 100 mg tablets (Tibotec Therapeutics, Titusville, N.J.) were obtained from a local drugstore. Itraconazole, formic acid, ammonium acetate and 1-methyl-2-pyrrolidinone (Lot#00796TK), Cremophore EL (Lot# BCBC 4069), mineral oil (Lot#066K0086), paraffin oil (Lot#0001445785) soybean oil (Lot#1253H), peanut oil (Lot#1237573 54605313), olive oil (Lot#1424412 50309P02), Tween 80 (Lot#049K0041) were purchased from Sigma, Inc. (St. Louis, Mo.). HPLC grade methanol (Mallinckrodt Baker Inc., Phillipsburg, N.J.) and acetonitrile (VWR International LLC, West Chester, Pa.) were purchased from the respective companies. Labrasol, Labrafac CC (Lot#3236BA2), Caproyle 90 (Lot#3254BM2), and Plurol oleique CC 497 (Lot#230) were obtained from Gattffossesas, Cedex, France. DMSO (Lot#46081638) and phosphoric acid (EMD Chemicals Inc., Gibbstown, N.J.), PEG 400 (Lot#960610P) (Wood Scientific Inc., Lot#960610), peppermint oil, lavender oil (Lot# W10161) (Spectrum Chemical MFG, Corp., Gardena, Calif.), and coriander oil (Lot# VL0201) and Tween 20 (Lot#85977) were purchased from PCCA (Houston, Tex.) or were purchased from the respective manufacturers. De-ionized water was obtained using a Milli-Q analytical deionization system (Millipore, Bedford, Mass.). Freshly obtained drug-free rat plasma was collected from male Sprague-Dawley rats (Harlan Laboratory Inc.) and stored at −80° C. prior to use. All other chemicals and solvents were of reagent grade and used without further purification.

Example 2

Evaluation of Etravirine Solubility in Various Media

The solubility of etravirine was determined in water, various oils and some organic solvents by phase solubility analysis. Excess drug was added into 20 ml screw-capped scintillation vials containing 5 ml of the tested solvents. The vials were rotated end-over-end at a constant speed on shaker (EBERBACH Corporation, Ann Arbor, Mich.) at room temperature for 3 days (72 hours). The samples were then subjected to centrifugation on a laboratory centrifuge at 13,000 rpm for 15 minutes. Aliquot of the supernatant was diluted with DMSO to the proper concentration before they were analyzed by high-performance liquid chromatography (HPLC) using UV detector.

Example 3

Analysis of Etravirine Using HPLC Method

The HPLC system involved Waters 600 pump, 2487 UV detector and 717 plus auto sampler (Waters Corporation, Milford, Mass.). Separations were done on a 4.6×150 mm, 3.5 μm XTerra MS-$C_{18}$ column (Waters Corporation, Milford, Mass.). The flow rate was set at 1 ml/min and the wavelength at 304 nm. Chromatographic data acquisition, peak integration and quantification were performed using the Empower software package by Waters Corporation. Mobile phase solution A consisted of 20 mM potassium dihydrogen phosphate aqueous solution and solution B consisted of acetonitrile (40% solution A+60% solution B). pH was adjusted to 3.2 using phosphoric acid. Solvents were regularly prepared prior to each series of analysis.

A stock solution of itraconazole (internal standard, IS) at 1 mg/ml (in acetonitrile) was diluted with acetonitrile to obtain a working solution of 25 ug/ml. Stock solution of etravirine in DMSO (1 mg/ml) was diluted with mobile phase (pH 3.2) for the preparation of working solutions at concentration ranging from 1 μg/ml to 100 μg/ml. These working solutions were diluted 1:10 with blank plasma to obtain the calibration samples ranging from 0.1 μg/ml to 10 μg/ml.

Example 4

Formulation Development

Solubility of etravirine in various solvents was summarized in Table 1. Etravirine is freely soluble in DMSO and 1-methyl-2-pyrrolidinone, soluble in PEG 400, Tween 80, Cremophore EL, Tween 20, and Labrasol®, slightly soluble in peanut oil, Caproyl 90, very slightly soluble in corn oil, soybean oil and olive oil, and practically insoluble in water.

Co-solvent formulations of etravirine were prepared by dissolving etravirine powder in small quantity of 1-methyl-2-pyrrolidinone. Surfactants such as LABRASOL® (caprylocaproyl macrogol-8 glyceride) were added followed by purified water. Various solvent compositions were tested for best suitable candidate. Each formulation was immediately tested for precipitation potential by 1:10 dilution of the formulation with purified water. Optimal formulations with no precipitation upon room temperature storage were further analyzed on etravirine stability in the formulation. Table 2 shows various formulation compositions of etravirine formulations.

Example 5

Stability of the Etrvirine Formulation

A long-term stability study was carried out to examine the physical stability of an optimal oral formulation of etravirine (Formulation #59). Three batches of the oral formulation #59 were prepared and stored at room temperature. Etravirine concentration in each batch was measured by HPLC using UV detection on the day of production and up to 21 months. Stability of etravirine in the formulation was summarized in Table 3.

Example 6

Animal Studies

All animal experiments and protocols were reviewed and approved by the Institutional Animal Care and Use Committee. Male Sprague-Dawley rats (250-350 g, Harlan Laboratory Inc., Indianapolis, Ind.) were housed in stainless steel cages and had free access to food and water. They were acclimated to the animal care facility for at least 7 days before the start of the study. To facilitate the withdrawal of timed, multiple blood samples from each animal, the right jugular vein of each animal was cannulated one day prior to drug administration. The cannulas were flushed daily with 0.5 mL sterile heparinized saline (100 units/ml). Under ketamine: acetopromazine:xylazine (50:3.3:3.3 mg/kg ip) anesthesia, silicone elastomer tubing (0.02×0.037 in) was inserted into the jugular vein, secured with a silk suture, and exteriorized in the dorsal infrascapular area. The surgical incision was prophylactically treated with nitrofurazone wound powder and closed with surgical staples.

Animals were allowed free access to food and water at all times. The jugular veins of the rats were cannulated under anesthesia the day before the study. All in vivo studies were initiated between 8:00 am and 9:00 am to eliminate possible circadian variation. The animals were fasted overnight with water allowed ad libitum before oral dosing.

The in vivo study consists of four rat groups. The first group was an intravenous group (n=6) which was given an intravenous 2.5 mg/kg administration of pure etravirine solution (3.5 mg/mL dissolved in DMSO). The second group is a reference group (n=5) which was given an oral 200 mg/kg administration of a suspension of the commercial Intelence® tablets in 1% Tween 80. The third group (n=8) is a liquid formulation of the present invention, designated formulation #59, which was given an oral administration of 25 mg/kg dose. The fourth group (n=8) is a liquid formulation of the present invention, designated formulation #59, which was given an oral administration of 50 mg/kg dose. Oral administration was performed using an animal feeding needle (18 in.×3 in. W; 2¼ mm Ball). Multiple blood samples (0.25 mL) were collected (from the jugular vein cannula) immediately before dosing and at 0.5, 1, 1.5, 2, 3, 4, 5, 6, 8, 10 and 24 hours after dosing. An aliquot of each plasma sample was stored at −70° C. pending LC-MS/MS assay.

Example 7

LC-MS/MS Determination of Etravirine Concentrations in Plasma

Etravirine concentrations in rat plasma was analyzed using a sensitive and accurate liquid chromatographic-tandem mass spectrometry (LC-MS/MS) method developed in the laboratory (10). Etravirine and the internal standard (itraconazole) were separated on a reverse phase XTerra MS-$C_{18}$ column (50 mm×2.1 mm, 3.5 µm) in conjunction with an XTerra® MS $C_{18}$ guard column (20 mm×3.9 mm, 3.5 µm). The mobile phase consisted of a 2 mM ammonium acetate aqueous solution containing 0.1% formic acid (Mobile Phase A) and a 0.1% formic acid in methanol solution (Mobile Phase B). A gradient elution starting with 40% mobile phase B was increased linearly to 100% Mobile Phase B over 5 minutes, kept constant at 100% Mobile Phase B for 2 min, and then decreased to 40% mobile phase B in 0.1 minutes, and this composition was maintained until the end of the run (8.0 minutes). The flow rate was set at 0.3 ml/minutes. The column effluent was monitored using a 3200 QTRAP® mass spectrum, which is a hybrid triple quadruple linear ion trap equipped with a Turbolonspray ion source. Pure nitrogen was generated by a Parker Balston Source 5000 Tri Gas Generator. The Ion Spry heater was maintained at 650° C. with both the nebulizer gas and heater gas set to 80 psi, respectively. Ion Spry needle voltage was set to 4500 V, the curtain gas was set to 10 psi, and the collision CAD gas was set to medium.

A series of etravirine working standard solutions were prepared by appropriate dilutions of the stock etravirine standard solution in DMSO (1 mg/mL) with a methanol:water (50:50, v/v) solution. Standard etravirine were then spiked in blank rat plasma to yield calibration standards in plasma over the concentration range of 1-100 ng/mL. Etravirine was extracted from plasma samples before the LC-MS/MS assay. Briefly, aliquot (100 µL) of plasma sample was mixed with 500 µL of ethyl acetate containing 200 ng/mL of the internal standard. The mixture was vortexed for 30 seconds, and centrifuged for 20 min. Then 450 µL of the supernatant was air dried, and the residual was reconstituted with 50% methanol in water, vortexed again, centrifuged and the supernatant was injected onto the LC-MS/MS system for quantification.

Example 8

Pharmacokinetic and Statistical Data Analysis

Non-compartmental pharmacokinetic parameters were determined by classical techniques using the WinNonlin computer program. The maximum plasma concentration of drug ($C_{max}$) was determined from the plasma drug concentration versus time profile. The terminal phase ($t_{1/2}$) rate constant was determined from the slope of the terminal linear segment of a semilogarithmic plot of plasma drug concentration vs. time. The total area under the plasma concentration-time curve (AUC) was determined by the trapezoidal rule using plasma drug concentration vs. time data from time zero to the last experimental time plus the excess area (from the last experimental time to time infinity). The excess area was calculated as $1.44 \times t_{1/2} \times$ plasma concentration at the last experimental time. The systemic clearance (CL) was determined as Dose F/AUC. The volume of distribution at steady-state ($V_{ss}$) was calculated as Dose/[AUMC/AUC$^2$], where AUMC is the area under the first moment plasma concentration time curve. Absolute bioavailability was calculated using $[(AUC_{oral} \times Dose_{i.v.})/(AUC_{i.v.} \times Dose_{oral})] \times 100\%$. Relative bioavailability was calculated using the equation $[(AUC_{formulation} \times Dose_{reference})/(Dose_{formulation} \times AUC_{reference})] \times 100\%$.

Statistical differences between the mean pharmacokinetic values were determined by Student t-test. The statistical analysis was performed in SYSTAT version 12.0 computer program. A P-value of less than 0.05 was considered as statistically significant.

Example 9

Development of Oral Formulation of Etravirine

Etravirine has low solubility among the tested oils and aqueous media, as shown in Table 1. Etravirine is practically insoluble in water with intrinsic solubility of 3.9 µg/mL in distilled water. Etravirine is freely soluble in DMSO and 1-methyl-2-pyrrolidinone, soluble in PEG 400, Tween 80, Cremophore EL, Tween 20, and Labrasol®, slightly soluble in peanut oil, Caproyl 90, very slightly soluble in corn oil, soybean oil and olive oil. Measured etravirine solubility in PEG 400 was 71.6 mg/mL, which is consistent with a value of 74 mg/mL reported in the scientific literature.

Various compositions of surfactant and co-surfactant were evaluated for an optimal oral formulation of etravirine. Tables 2A-2B summarize such compositions. Etravirine concentrations in these formulations ranged from 5 mg/mL to 10 mg/mL. Most of these formulations were clear solutions at the beginning and the drug precipitated within 24 hours at room temperature.

TABLE 1

Solubility of Etravirine in Various Medium at Room Temperature

| Vehicle | Drug Solubility (mg/mL) |
|---|---|
| Water | 0.00397 |
| PEG 400 | 71.6 ± 1.45 |
| 1-methyl-2-pyrrolidinone | 458.4 |
| Labrasole | 61.0 |
| Tween 80 | 49.7 ± 0.41 |
| Tween 20 | 55.8 ± 0.87 |
| Cremophore EL | 46.0 ± 0.69 |
| Pluro oleique CC 497 | 1.04 ± 0.02 |
| Labrafac CC | 1.04 ± 0.01 |
| Capryol 90 | 5.42 ± 0.06 |
| Peanut Oil | 2.19 |
| Paraffin Oil | 0.009 |
| Linseed Oil | 0.79 |
| Lavender Oil | 1.23 |
| Corn Oil | 0.42 |
| Mineral Oil | 0.004 |
| Soybean Oil | 0.31 |
| Olive Oil | 0.22 |
| Coriander Oil | 0.74 |

TABLE 2A

Compositions of Selected Oral Etravirine Liquid Formulations

| Formula | Drug (mg) | DMSO (µL) | PEG 400 (µL) | Tween 80 (µL) | Cremophor EL (µL) | 1-methyl-2-pyrrolidinones (µL) | Tween 20 (µL) |
|---|---|---|---|---|---|---|---|
| 1 | 10 | 50 | 450 | | | | |
| 2 | 10 | 50 | | | 300 | | |
| 4 | 10 | 50 | | 450 | | | |
| 6 | 10 | 50 | | | | | 450 |
| 7 | 10 | 50 | | 300 | | | |
| 9 | 10 | 25 | | | | | |
| 10 | 10 | 50 | 100 | 350 | | | |
| 24 | 10 | | | | | | |
| 29 | 5 | | | | | | |
| 39 | 5 | | | | | | |
| 45 | 10 | | | | | 100 | |
| 50 | 10 | | | | | | |
| 58 | 5 | | | | | 35 | |
| 59** | 5 | | | | | 35 | |

TABLE 2B

| Formula | Drug (mg) | Labrasol (µL) | Capryol 90 (µL) | Plurolo-leique (µL) | Labrafac (µL) | H2O (µL) | Appearance 1 h | 5 h | 24 h |
|---|---|---|---|---|---|---|---|---|---|
| 1 | 10 | | | | | 500 | ppt | ppt | ppt* |
| 2 | 10 | | | | | 500 | clear | ppt | ppt |
| 4 | 10 | | | | | 500 | clear | ppt | ppt |
| 6 | 10 | | | | | 500 | clear | ppt | ppt |
| 7 | 10 | 150 | | | | 500 | clear | ppt | ppt |
| 9 | 10 | 380 | | 95 | | 500 | clear | ppt | ppt |
| 10 | 10 | | | | | 500 | clear | clear | ppt |
| 24 | 10 | 250 | | | 250 | 500 | clear | clear | ppt |
| 29 | 5 | 700 | | | | 300 | clear | clear | clear |
| 39 | 5 | 500 | | 70 | 30 | 400 | clear | clear | ppt |
| 45 | 10 | 200 | 100 | | 100 | 500 | clear | clear | ppt |
| 50 | 10 | 400 | 100 | | | 400 | clear | clear | ppt |
| 58 | 5 | 500 | | | | 465 | clear | clear | clear |
| 59** | 5 | 465 | | | | 500 | clear | clear | clear |

*Precipitation;
**The formulation was selected for further long-term stability and oral bioavailability testing.

The present invention demonstrated that a co-solvent system (designated herein as formulation #59) consisting of 1-methyl 2-pyrrolidinone, LABRASOL®, and water at 3.5:46.5:50 (v/v/v) ratio showed a 5 mg/mL drug solubility in 50% of an aqueous medium, and no drug precipitation after storage. Thus, this formulation was selected for further long-term drug stability testing as well as in vivo bioavailability evaluations.

Example 10

Evaluation of Formulation Stability

Etravirine stability in the dosage formulation #59 was evaluated for long-term storage at room temperature. There was no significant degradation of etravirine from three separate batches of the formulation after 21-month storage at room temperature. Following the 21 month storage, there was no sign of any drug precipitation (Table 3).

TABLE 3

Stability of Etravirine in the Dosage Formulation #59 at Room Temperature

| Storage Time | Mean ± SD Etravirine Concentration (mg/mL) in the Formulation #59 |
| --- | --- |
| Immediately After the Preparation | 4.922 ± 0.044 |
| 1 month at room temperature | 5.153 ± 0.028 |
| 3 months at room temperature | 4.978 ± 0.097 |
| 9 months at room temperature | 5.013 ± 0.010 |
| 21 months at room temperature | 4.977 ± 0.474 |

Example 11

Pharmacokinetic Analysis

Figure 2:
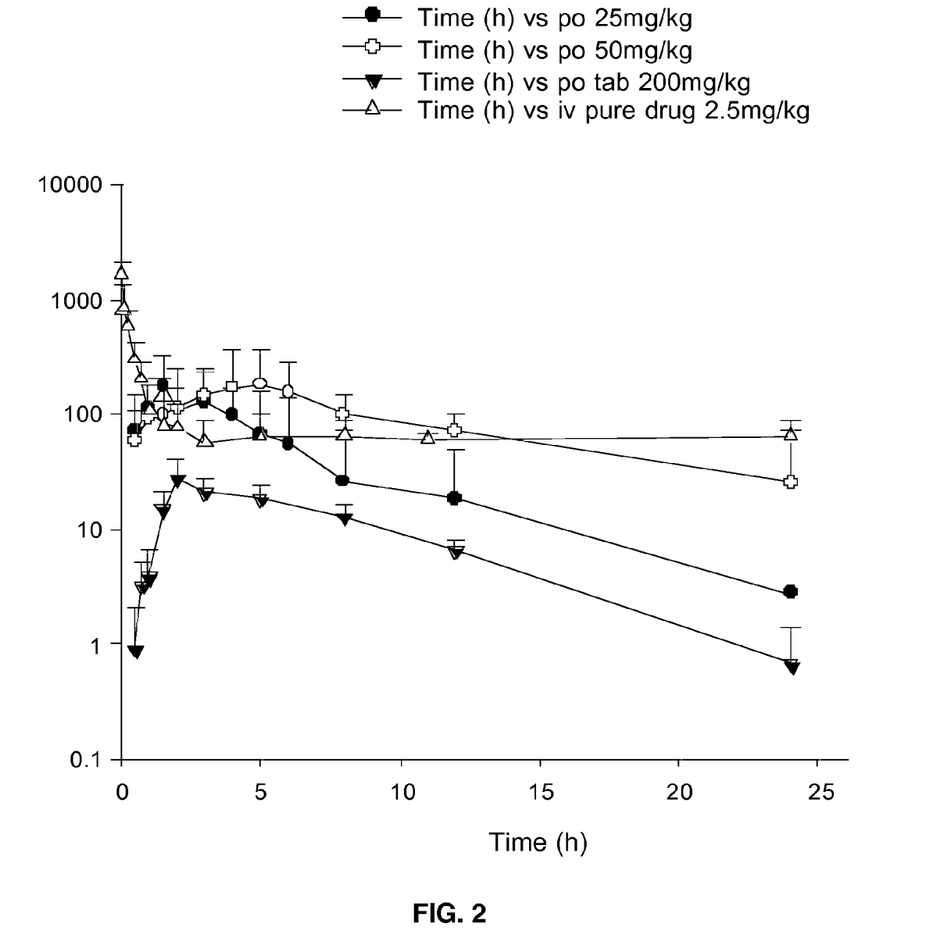
FIG. 2 shows the mean (+SD) comparative plasma etravirine concentration versus time profiles after oral administration of a 25-mg/kg or 50 mg/kg dose of the formulation of the present invention or a 200 mg/kg dose of Intelence® to male Sprague-Dawley rats.

In vivo pharmacokinetic studies were conducted to evaluate whether the oral formulation (#59) of etravirine of the present invention had comparable oral bioavailability to the brand 100-mg Intelence® tablets. FIG. 2 showed mean plasma concentrations versus time curve of etravirine following the drug administrations. The time to reach maximum plasma drug concentration was about 2 hours post administration for the reference group, whereas, the time for the formulation groups ranged from 4-6 hours post drug administration. Mean plasma concentrations were higher in the formulation groups as compared with the reference group.

Pharmacokinetic parameters are summarized in Table 4 and statistical comparisons are performed after dose normalization. There was an 8-fold increase in the maximum plasma concentration ($C_{max}$) and 5-fold increase in the area under the curve (AUC) for 25-mg/kg formulation group as compared with the reference commercial Intelence® group. The terminal elimination half-lives for oral administered groups were significantly longer than that of intravenously administered group, which is a flip-flop pharmacokinetic phenomena, i.e., the actual terminal elimination half-life of etravirine is shorter than its GI absorption half-life, and hence the observed terminal elimination half-life of etravirine after oral administration actually represents the GI absorption half-life of the drug. This observation was consistent with the fact that etravirine is a poorly permeable drug in the GI tract and consequently the terminal elimination half-life is a reflection of its GI absorption half-life.

TABLE 4

Pharmacokinetics of Etravirine following Intravenous Administration of Pure Etyravirine Solution or Oral Administration of Formulation #59 versus the Commercial Intelence ® Product to Male Sprague-Dawley Rats

| Parameter[a] | IV 2.5 mg/kg of Etravirine | Oral 200 mg/kg of Intelence ® | Oral 25 mg/kg of Formulation #59 | Oral 50 mg/kg of Formulation #59 |
| --- | --- | --- | --- | --- |
| No. of Animals | 6 | 5 | 8 | 8 |
| Tmax (h) | — | | | |
| $C_{max}$ (ng/mL) | 2364 ± 1122 | 27.97 ± 11.9 | 222.3 ± 150 | 228.2 ± 169 |
| AUC (ng h/mL) | 1656 ± 498 | 194.1 ± 74.2 | 1047 ± 654 | 1664 ± 1107 |
| $T_{1/2}$ (h) | 1.14 ± 0.91 | 5.65 ± 2.81 | 3.15 ± 1.76 | 4.08 ± 1.43 |
| $V_{ss}/F$ (mL/kg) | 2.25 ± 1.42 | 8.0 ± 5.7 | 127 ± 79 | 207 ± 107 |
| CL/F (mL/hr/kg) | 1.58 ± 0.57 | 0.92 ± 0.17 | 29.0 ± 10.4 | 36.3 ± 16.1 |
| $F_{absolute}$ | — | 0.145% | 6.32% | 5.02% |
| $F_{relative}$ | — | — | 4.315% | 3.429% |

[a]N = number of rats employed;

$T_{1/2}$ = terminal biological half-life;

AUC = total area under the plasma concentration versus time curve;

$C_{max}$ = predicted maximum drug concentration in plasma;

$V_{ss}$ = volume of distribution at steady-state;

CL = total body clearance.

Absolute bioavailability ($F_{absolute}$) was calculated using (AUC$_{oral}$ × Dose $_{i.v}$)/(AUC$_{i.v}$ × Dose$_{oral}$) × 100.

Relative bioavailability ($F_{relative}$) was calculated using the equation (AUC$_{formulation}$ × Dose$_{reference}$)/(Dose$_{formulation}$ × AUC$_{reference}$).

The absolute oral bioavailability of etravirine was calculated as 0.15% for the commercial Intelence® tablet. Absolute oral bioavailability for the formulation #59 was found to be 6.32% at 25-mg/kg dose and 5.02% at 50 mg/kg dose. As a result, the relative oral bioavailability of the #59 formulation compared with the reference tablet was 43 and 34 at 25-mg/kg and 50-mg/kg dose, respectively. Therefore, the formulation #59 achieved as much as 43-fold increase in the drug availability.

Example 12

Acute Toxicity

No signs of discomfort or any cardiovascular or respiratory disorders were observed in all animals after the drug administrations and throughout the study period. There was no change in body weight monitored for a 7-day period after drug administrations.
Discussion The present invention demonstrates the development of a co-solvent formulation of etravirine suitable for oral administration. In a preferred form, the formulation contains 5 mg/mL of etravirine dissolved in 3.5% 1-methyl-2-pyrrolidinone, 46.5% LABRASOL®, and 50% water. The formulation was found to be stable after 21 month storage at room temperature. The drug formulation was successfully administered to rats without signs of acute toxicity. Pharmacokinetic study also showed an over 40 times superior oral bioavailability of the formulation as compared with the marketed INTELENCE® Table formulation.

The following references were cited herein:
1. Johnson et al., *Clin. Infect. Dis.,* 48:1123-8, 2009.
2. Adams et al., *Ann. Pharmacother.,* 44:157-65, 2010.
3. INTELENCE® (etravirine) Tablets Package Insert, 2008.
4. Scholler-Gyure et al., Clinical pharmacokinetics and pharmacodynamics of etravirine. *Clin. Pharmacokinet.,* 48:561-74, 2009.
5. Crauwels et al., *Clin. Pharmacokinet.,* 49:67-8, 2010.
6. European Medicines Agency, Doc. Ref. EMEA/CHMP/43952/2008.
7. Kakuda et al., TMC125 in combination with other medications: summary of drug-drug interactions. 8th International Congress on Drug Therapy in HIV Infection, November 2006; Glasgow, UK.
8. Schöller-Gyüre et al., Effect of food on the oral bioavailability of the phase III formulation of TMC125. 7th International Workshop of Clinical Pharmacology; April 2006; Lisbon, Portugal.
9. Amidon et al., *Pharm. Res.* 12:413-20, 1995.
10. Abobo et al., J. Chromotogr. B, 878:3181-6, 2010.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A pharmaceutical liquid formulation of etravirine, said formulation comprising:
   etravirine;
   a dipolar aprotic solvent;
   a non-ionic water dispersible surfactant; and
   water.

2. The pharmaceutical formulation of claim 1, wherein said etravirine is contained in said formulation in a concentration range of from about 5 mg/mL to about 10 mg/mL.

3. The pharmaceutical formulation of claim 1, wherein said dipolar aprotic solvent is selected from the group consisting of 1-methyl-2-pyrrolidinone, dimethylformamide, dimethylacetamide, and dimethyl sulfoxide.

4. The pharmaceutical formulation of claim 3, wherein said 1-methyl-2-pyrrolidinone, dimethylformamide, dimethylacetamide, or dimethyl sulfoxide are contained in said formulation in a concentration of from about 0.5% to about 10%.

5. The pharmaceutical formulation of claim 1, wherein said nonionic surfactant comprises polyethylene glycol esters, a glyceride fraction and polyethylene glycol.

6. The pharmaceutical formulation of claim 5, wherein said nonionic surfactant is selected from the group consisting of caprylocaproyl macrogol-8 glyceride, polyoxyl 40 hydrogenated castor oil, polyoxyl 60 hydrogenated castor oil, polyoxyl 35 castor oil, polyoxyl 5 castor oil, polyoxyl 9 castor oil, polyoxyl 15 castor oil, d-α-tocopheryl polyethylene glycol 1000 succinate (TPGS), polyethylene glycol (15)-hydroxystearate, and PEG 300 caprylic/capric glycerides.

7. The pharmaceutical formulation of claim 6, wherein said caprylocaproyl macrogol-8 glyceride is contained in said formulation in a concentration of from about 40% to about 50%.

8. The pharmaceutical formulation of claim 7, wherein said caprylocaproyl macrogol-8 glyceride is contained in said formulation in a concentration of from about 46%.

9. The pharmaceutical formulation of claim 7, wherein said formulation contains 5 mg/mL of etravirine dissolved in 3.5% 1-methyl-2-pyrrolidinone, 46.5% caprylocaproyl macrogol-8 glyceride, and 50% water.

10. The pharmaceutical formulation of claim 1, wherein the formulation is suitable for oral administration.

11. A method of treating an individual infected with HIV, comprising the step of administering the pharmaceutical formulation of claim 1 to said individual.

12. A pharmaceutical liquid formulation of etravirine, said formulation comprising:
   etravirine;
   a non-ionic water dispersible surfactant; and
   water.

13. The pharmaceutical formulation of claim 12, wherein said etravirine is contained in said formulation in a concentration range of from about 5 mg/mL to about 10 mg/mL.

14. The pharmaceutical formulation of claim 12, wherein said nonionic surfactant comprises polyethylene glycol esters, a glyceride fraction and polyethylene glycol.

15. The pharmaceutical formulation of claim 14, wherein said nonionic surfactant is selected from the group consisting of caprylocaproyl macrogol-8 glyceride, polyoxyl 40 hydrogenated castor oil, polyoxyl 60 hydrogenated castor oil, polyoxyl 35 castor oil, polyoxyl 5 castor oil, polyoxyl 9 castor oil, polyoxyl 15 castor oil, d-α-tocopheryl polyethylene glycol 1000 succinate (TPGS), polyethylene glycol (15)-hydroxystearate, and PEG 300 caprylic/capric glycerides.

16. The pharmaceutical formulation of claim 15, wherein said caprylocaproyl macrogol-8 glyceride is contained in said formulation in a concentration of from about 40% to about 60%.

17. The pharmaceutical formulation of claim 16, wherein said caprylocaproyl macrogol-8 glyceride is contained in said formulation in a concentration of from about 50%.

18. The pharmaceutical formulation of claim 16, wherein said formulation contains 5 mg/mL of etravirine dissolved in 50% caprylocaproyl macrogol-8 glyceride, and 50% water.

19. The pharmaceutical formulation of claim 12, wherein the formulation is suitable for oral administration.

20. A method of treating an individual infected with HIV, comprising the step of administering the pharmaceutical formulation of claim 14 to said individual.

21. A pharmaceutical liquid formulation of etravirine, said formulation comprising:
    etravirine;
    1-methyl-2-pyrrolidinone;
    a non-ionic water dispersible surfactant; and
    water.

22. The pharmaceutical formulation of claim 21, wherein said etravirine is contained in said formulation in a concentration range of from about 5 mg/mL to about 10 mg/mL.

23. The pharmaceutical formulation of claim 21, wherein said 1-methyl-2-pyrrolidinone is contained in said formulation in a concentration of from about 0.5% to about 10%.

24. The pharmaceutical formulation of claim 21, wherein said nonionic surfactant comprises polyethylene glycol esters, a glyceride fraction and polyethylene glycol.

25. The pharmaceutical formulation of claim 24, wherein said nonionic surfactant is selected from the group consisting of caprylocaproyl macrogol-8 glyceride, polyoxyl 40 hydrogenated castor oil, polyoxyl 60 hydrogenated castor oil, polyoxyl 35 castor oil, polyoxyl 5 castor oil, polyoxyl 9 castor oil, polyoxyl 15 castor oil, d-α-tocopheryl polyethylene glycol 1000 succinate (TPGS), polyethylene glycol (15)-hydroxystearate, and PEG 300 caprylic/capric glycerides.

26. The pharmaceutical formulation of claim 24, wherein said caprylocaproyl macrogol-8 glyceride is contained in said formulation in a concentration of from about 40% to about 50%.

27. The pharmaceutical formulation of claim 26, wherein said caprylocaproyl macrogol-8 glyceride is contained in said formulation in a concentration of from about 46%.

28. A method of treating an individual infected with HIV, comprising the step of administering the pharmaceutical formulation of claim 21 to said individual.

* * * * *